United States Patent
Riondel et al.

(10) Patent No.: US 7,151,190 B1
(45) Date of Patent: Dec. 19, 2006

(54) METHOD FOR MAKING AQUEOUS SOLUTIONS OF UNSATURATED QUATERNARY AMMONIUM SALTS

(75) Inventors: Alain Riondel, Forbach (FR); Gilles Herbst, Spicheren (FR); Marc Esch, Freyming-Merlebach (FR)

(73) Assignee: Arkema France (formerly Atofina), Puteaux (FR)

( * ) Notice: Subject to any disclaimer, the term of this patent is extended or adjusted under 35 U.S.C. 154(b) by 0 days.

(21) Appl. No.: 09/889,699

(22) PCT Filed: Jan. 20, 2000

(86) PCT No.: PCT/FR00/00123

§ 371 (c)(1),
(2), (4) Date: Sep. 25, 2001

(87) PCT Pub. No.: WO00/43347

PCT Pub. Date: Jul. 27, 2000

(30) Foreign Application Priority Data

Jan. 21, 1999 (FR) .................................. 99 00642

(51) Int. Cl.
*C07C 69/533* (2006.01)
(52) U.S. Cl. ........................................ 560/221; 560/222
(58) Field of Classification Search ................ 560/222, 560/221
See application file for complete search history.

(56) References Cited

U.S. PATENT DOCUMENTS

| | | | |
|---|---|---|---|
| 4,745,214 A | 5/1988 | Hess et al. | |
| 5,260,480 A | 11/1993 | Lacroix et al. | |
| 5,912,383 A | 6/1999 | Riondel et al. | |
| 5,919,974 A | 7/1999 | Riondel | |

FOREIGN PATENT DOCUMENTS

| | | |
|---|---|---|
| EP | 0250325 | 12/1987 |
| EP | 0329512 | 8/1989 |
| WO | WO 8907588 | 8/1989 |

*Primary Examiner*—Taofiq Solola
(74) *Attorney, Agent, or Firm*—Millen, White, Zelano & Branigan, P.C.

(57) ABSTRACT

The invention concerns a method for making aqueous solutions of unsaturated quaternary ammonium salts of formula (I) by reacting, in the presence of water, N,N-dimethylaminoethyl acrylate with a quaternizing agent of formula (II): R—Cl, said method is characterized in that it consists in: (a) in a closed reactor containing 5 60 wt. % of N,N-dimethylaminoethyl acrylate required for the reaction and which has been pressurized with air or depleted air at 0.5 to 3 bars, carrying out the reaction by continuously introducing, at a temperature ranging between 35 to 65° C., the quaternizing agent (II), and water, and finally the remaining N,N-dimethylaminoethyl acrylate, until the desired concentration of salt (I) in the water is reached, the water being introduced only when 0–20 wt. % of the amount required for the quaternizing agent (II) reaction has been added; the introduction of the remaining N,N-dimethylaminoethyl acrylate starting only when 20–80 wt. % required for the quaternizing agent (II) reaction has been added; and the pressure at the end of the reaction capable of reaching 9 bars; then (b) in depressurizing while maintaining the oxygen content constant by simultaneous introduction of air and, after returning to atmospheric pressure, eliminating the residual quaternizing agent. In formule (I) and (II). R=methyl or benzyl.

23 Claims, No Drawings

METHOD FOR MAKING AQUEOUS SOLUTIONS OF UNSATURATED QUATERNARY AMMONIUM SALTS

The present invention relates to the manufacture of aqueous solutions of unsaturated quaternary ammonium salts (hereinafter denoted quaternary salts) corresponding to the following formula (I):

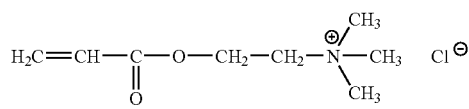

in which R represents methyl or benzyl, by reaction, in the presence of water, of N,N-dimethylaminoethyl acrylate (DAMEA) with a quaternizing agent of formula (II):

in which R is as defined above.

Aqueous solutions of quaternary salts (I) are used to prepare polymers intended to act as cationic flocculents in water treatment.

European patent EP-B-250 325 discloses a process for the preparation of aqueous solutions of quaternary salts, including those of formula (I) according to which process, in the presence of at least one polymerization inhibitor:

in a first stage (a), DAMEA is reacted with 5 to 20% by weight of the amount by weight of the quaternizing agent necessary for the reaction or, according to an alternative form (a'), with 5 to 20% by weight, with respect to the weight of the DAMEA, of an aqueous solution of quaternary salts, which solution comprises from 50 to 85% by weight of quaternary salts; and in a second stage (b), water and the quaternizing agent are continuously added until the desired concentration of quaternary salts in the water is obtained.

During stages (a) and (b), the temperature is maintained at a value of between 30 and 60° C. Furthermore, during stages (a) and (b) and in particular near the end of the reaction, a stream of oxygenated gas is maintained in the reaction medium such that the ratio by volume (or volumetric throughput) of total gas at the outlet of the reactor to the volume (or volumetric throughput) of oxygen introduced at the inlet of this same reactor is less than 100.

This process makes it possible to prepare aqueous solutions of quaternary salts which have a stability at ambient temperature of greater than one year. However, a particularly high content of impurities, in particular of

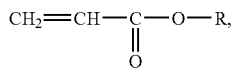

of

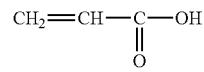

and of DAMEA, is found in these solutions. In addition, this process requires relatively long reaction times, which represents an obvious economic disadvantage.

A process intended to reduce the formation of the impurities during the quaternization reaction was then provided in international application WO 89/07 588. In accordance with this process, the reaction is carried out at a temperature of between 10 and 80° C., and (a) in a first stage, all or a portion of the quaternizing agent necessary for the reaction is introduced into the reactor, this agent being in the liquid state under the reaction conditions, (b) subsequently, the DAMEA is added, and (c) as soon as 0 to 30% of the stoichiometry of the DAMEA has been introduced into the reactor, the remainder of the quaternizing agent, the remainder of the DAMEA and the water are continuously and simultaneously added until the desired concentration of quaternary salts is obtained, (d) and, in the case where the quaternizing agent is introduced in the gaseous state at the reaction temperature, the reaction is carried out in the presence of oxygen and a pressure is applied so that the quaternizing agent is liquid at the reaction temperature, and, at the end of the reaction, the pressure is gradually reduced to atmospheric pressure and simultaneously a ratio as volumetric throughput of total gas at the outlet of the reactor to the volumetric throughput of oxygen introduced into the reactor of less than 100 is imposed.

The above process according to WO 89/07 588 introduces significant improvement to the process according to EP-B-250 325. However, it transpired that the purity with which the quaternary salts are obtained is still insufficient. Thus, during the reaction of DAMEA with $CH_3Cl$ in aqueous medium, resulting in the salt also denoted subsequently by the abbreviation ADAMQUAT MC, the dimer of ADAMQUAT MC, represented by the formula (1):

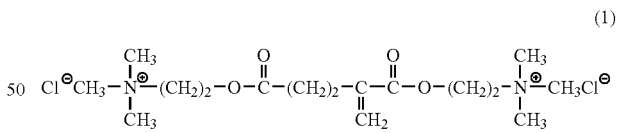

is formed as impurities, in addition to acrylic acid (AA), formed by hydrolysis of DAMEA.

By virtue of a series of tests of reactivity with regard to polymerization, it was possible to demonstrate that these impurities affected the quality of the cationic polymers derived from ADAMQUAT.

The applicant company has thus looked for operating conditions for the preparation of aqueous solutions of the salt of formula (I) which are capable of minimizing the abovementioned impurities, so as to provide a salt (I) in aqueous solution of very high analytical quality.

This novel process, which thus forms the subject matter of the present invention, is characterized in that:

(a) the reaction is carried out in a closed reactor, which comprises 5–60% of the amount by weight of DAMEA necessary for the reaction and which has been pressurized by air or depleted air to 0.5 to 3 bar, by continuously introducing, at a temperature of 35 to 65° C., in particular of 40 to 60° C., on the one hand, the quaternizing agent (II) and, on the other hand, the water and finally the remaining DAMEA, until the desired concentration of salt (I) in the water is obtained, the start of the introduction of the water beginning when 0–30%, in particular 10–20%, of the amount by weight of the quaternizing agent (II) necessary for the reaction has been added;

the start of the introduction of the remaining DAMEA beginning when 20–80%, in particular 30–70%, of the amount by weight of the quaternizing agent (II) necessary for the reaction has been added; and it being possible for the pressure at the end of the reaction to reach 9 bar, in particular 4 to 7 bar; then (e) the reactor is depressurized while keeping the oxygen content constant by simultaneous introduction of air and, after returning to atmospheric pressure, the residual quaternizing agent is removed, for example by stripping with air.

In accordance with other specific characteristics of the process according to the invention:

the quaternizing agent is introduced over a period of time of 1–7 hours, the water over a period of time of 1–8 hours and the remaining DAMEA over a period of time of 2–8 hours;

the reaction is carried out with a molar ratio of the quaternizing agent to the DAMEA of 1 to 1.1, preferably of 1 to 1.05;

the reaction is carried out with a mean ratio of water/quaternizing agent throughput of 0.2–1.5, in particular of 0.4–1, a mean ratio of remaining DAMEA/quaternizing agent throughput of 2.5–5, in particular 3–4, and a mean ratio of water/remaining DAMEA throughput of 0.2–1.2, in particular of 0.3–0.9.

The process according to the invention makes it possible in particular to prepare aqueous solutions having a concentration of quaternary salts (I) of 50 to 85% by weight and comprising very low amounts of impurities, as illustrated in Table 1 below.

Furthermore, the process according to the present invention can be carried out in the presence of at least one stabilizer, which can be chosen from 3,5-di(tert-butyl)-4-hydroxytoluene, hydroquinone methyl ether, hydroquinone, catechol, tert-butylcatechol, phenothiazine and mixtures of these stabilizers, the content of stabilizing agent(s) being in particular from 20 to 2000 ppm, preferably from 100 to 1200 ppm, with respect to the aqueous solution of quaternary salt (I).

In addition, at least one sequestering agent for metals chosen in particular from diethylene-triaminepentaacetic acid, the pentasodium salt of diethylenetriaminepentaacetic acid, N-(hydroxyethyl)-ethylenediaminetriacetic acid and the trisodium salt of N-(hydroxyethyl)ethylenediaminetriacetic acid can be added to the reaction medium, the content of sequestering agent(s) being in particular from 1 to 100 ppm, preferably from 5 to 30 ppm, with respect to the aqueous solution of quaternary salt (I).

Generally, the sequestering agents are added in the form of an aqueous solution as they are generally available in this form. Thus, the pentasodium salt of diethylenetriaminepentaacetic acid sold under the name Versenex 80 is provided in the form of an approximately 40% by weight aqueous solution.

The following examples illustrate the present invention without, however, limiting the scope thereof. From these examples, the percentages are by weight, unless otherwise indicated.

EXAMPLE 1

200 g of DAMEA (i.e. 46.6% of all the DAMEA) were charged to a 1 l jacketed glass reactor, specially designed to withstand pressure, equipped with a temperature probe, with a gas/liquid specific stirrer (turbine with a hollow shaft), with a valve tared at 10 bar, with a bursting disc and with dip pipes for the introduction of the various reactants. The reactor was closed and then pressurized with 1 bar of depleted air. Stirring and heating were begun.

As soon as the temperature reached 40° C. (process temperature=47° C.), the introduction of $CH_3Cl$ was begun at a throughput of 70 g/h. When 35 g of $CH_3Cl$ were introduced, the introduction of water was begun at a throughput of 28.6 g/h. After reacting for 1 h, the $CH_3Cl$ throughput was brought back to 20.9 g/h. The introduction of the remainder of the DAMEA (i.e. 229 g) was begun at a throughput of 76.3 g/h after reacting for 1.5 h. At the end of the reaction, the reactor was brought back to atmospheric pressure using the following protocol:

degassing the excess $CH_3Cl$ for 30 minutes with simultaneous introduction of air into the charge (throughput: 3 Sl/h);

gradual return to atmospheric pressure, and the traces of $CH_3Cl$ were removed by stripping with air (throughput: 5 Sl/h) for 30 minutes.

The reactor was subsequently cooled and then emptied. 710 g of ADAMQUAT MC 80 were recovered and were analyzed by high performance liquid chromatography (HPLC) to determine the contents of AA and of compound (1). The results are reported in Table 1.

The durations of the various phases of the reaction were as follows:

| | |
|---|---|
| $CH_3Cl$ introduction | 5.25 h |
| $H_2O$ introduction | 5 h |
| DAMEA introduction | 3 h |
| degassing | 0.5 h |
| stripping | 0.5 h | i.e. a total duration of approximately 6.75 h.

The throughput ratios used were:

| | |
|---|---|
| $H_2O/CH_3Cl$ | 0.41 for the first hour, then 1.37 for the remainder of the reaction; |
| $H_2O$/DAMEA | 0.37 |
| DAMEA/$CH_3Cl$ | 3.64. |

EXAMPLE 2

The preparation was carried out as in Example 1, except that the CH₃Cl throughput was increased.
The results are also reported in Table 1.

TABLE 1

[Ch₃Cl]/[DAMEA] = 1.05; T = 47° C.; Maximum pressure: 6 bar; DAMEA: 429 g (3 mol); CH₃Cl = 15 g (3.15 mol)

| Example | Mass of the crude reaction mixture (g) | Duration of introduction of CH₃Cl (h) | $H_2O$/ DAMEA | DAMEA/ $CH_3Cl$ | $H_2O$/ $CH_3Cl$ | HPLC analysis (ppm) | | QUATS (%) |
|---|---|---|---|---|---|---|---|---|
| | | | | | | AA | ADAMQUAT MC dimer of formula (1)* | |
| 1 | 710 | 5.25 | 0.37 | 3.65 | 0.4 then 1.37 | 426 | 407 | 81 |
| 2 | 724 | 4 | " | " | " | 418 | 277 | 82.8 |

*Content of ADAMQUAT MC dimer of formula (1), expressed arbitrarily as AA

The invention claimed is:

1. A process for preparing an aqueous solution of unsaturated quaternary ammonium salt of formula I

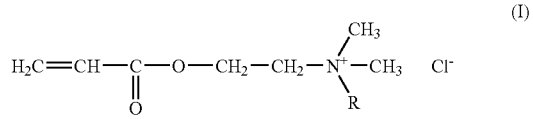

in which R represents a methyl or benzyl radical, comprising reacting, in the presence of water, N,N-dimethyl-aminoethyl acrylate (DAMEA) with a quaternizing agent of formula II

in which R is as defined above, wherein:
(a) the reaction is carried out in a closed reactor, which comprises 5–60% of the amount by weight of the DAMEA necessary for the reaction and which has been pressurized by air or depleted of air to 0.5 to 3 bar, by continuously introducing, at a temperature of 35 to 65° C., the quaternizing agent of formula (II) and the water and finally the remaining DAMEA, until the desired concentration of the salt of the compound of formula (I) in the water is obtained, wherein
the start of the introduction of the water beginning when 0–30% of the amount by weight of the quaternizing agent of formula (II) necessary for the reaction has been added;
the start of the introduction of the remaining DAMEA begins when 20–80% of the amount by weight of the quaternizing agent of formula (II) necessary for the reaction has been added; and
it being possible for the pressure at the end of the reaction to reach 9 bar; then
(b) the reactor is depressurized while keeping the oxygen content constant by simultaneous introduction of air and, after returning to atmospheric pressure, the residual quaternizing agent is removed, and
wherein no stabilizer is used in the process as a reagent and optionally a sequestering agent is used as a reagent.

2. The process as claimed in claim 1, wherein the reaction is carried out at a temperature of 40 to 60° C.

3. The process as claimed in claim 1, wherein the pressure at the end of the reaction reaches 4 to 7 bar.

4. The process as claimed in claim 1, wherein the introduction of the water is started when 10–20% of the amount by weight of the quaternizing agent of formula (II) necessary for the reaction has been added.

5. The process as claimed in claim 1, wherein the introduction of the remaining DAMEA is started when 30–70% of the amount by weight of the quaternizing agent of formula (II) necessary for the reaction has been added.

6. The process as claimed in claim 1, wherein the quaternizing agent is introduced over a period of time of 1–7 hours, the water over a period of time of 1–8 hours and the remaining DAMEA over a period of time of 2–8 hours.

7. The process as claimed in claim 1, wherein the reaction is carried out with a molar ratio of the quaternizing agent to the DAMEA of 1 to 1.1.

8. The process as claimed in claim 1, wherein the reaction is carried out with a mean ratio of water/quaternizing agent throughput of 0.2–1.5; a mean ratio of remaining DAMEA/quaternizing agent throughput of 2.5–5; and a mean ratio of water/remaining DAMEA throughput of 0.2–1.2.

9. The process as claimed in claim 1, which results in an aqueous solution having a concentration of quaternary salt of formula (I) of 50 to 85% by weight.

10. The process as claimed in claim 1, carried out in the presence of at least one sequestering agent for metals which is diethylene-triaminepentaacetic acid, the pentasodium salt of diethylenetriaminepentaacetic acid, N-(hydroxyethyl)-ethylenediaminetriacetic acid or the trisodium salt of N-(hydroxyethyl)ethylenediaminetriacetic acid, the content of sequestering agent(s) being 1 to 100 ppm, with respect to the aqueous solution of quaternary salt of formula (I).

11. The process as claimed in claim 1, wherein the residual quaternizing agent is removed by stripping with air.

12. The process as claimed in claim 1, wherein the reaction is carried out with a molar ratio of the quaternizing agent to the DAMEA of 1 to 1.05.

13. The process as claimed in claim 1, carried out in the presence of at least one sequestering agent for metals which is diethylene-triaminepentaacetic acid, the pentasodium salt of diethylenetriaminepentaacetic acid, N-(hydroxyethyl)-ethylenediaminetriacetic acid or the trisodium salt of N-(hydroxyethyl)ethylenediaminetriacetic acid, the content of sequestering agent(s) being 5 to 30 ppm, with respect to the aqueous solution of quaternary salt of formula (I).

14. The process of claim 1 for preparing an aqueous solution of unsaturated quaternary ammonium salt of formula I

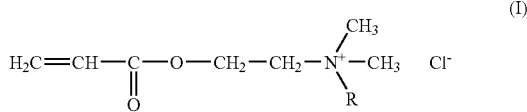

in which R represents a methyl or benzyl radical, comprising reacting, in the presence of water, N,N-dimethyl-aminoethyl acrylate (DAMEA) with a quaternizing agent of formula II R—Cl (II)

in which R is as defined above, wherein:
(a) the reaction is carried out in a closed reactor, which comprises 5–60% of the amount by weight of the DAMEA necessary for the reaction and which has been pressurized by air or depleted of air to 0.5 to 3 bar, by continuously introducing, at a temperature of 35 to 65° C., the quaternizing agent of formula (II) and the water and finally the remaining DAMEA, until the desired concentration of the salt of the compound of formula (I) in the water is obtained, wherein the start of the introduction of the water beginning when 0–30% of the amount by weight of the quaternizing agent of formula (II) necessary for the reaction has been added;

the start of the introduction of the remaining DAMEA begins when 20–80% of the amount by weight of the quaternizing agent of formula (II) necessary for the reaction has been added; and it being possible for the pressure at the end of the reaction to reach 9 bar; then
(b) the reactor is depressurized while keeping the oxygen content constant by simultaneous introduction of air and, after returning to atmospheric pressure, the residual quaternizing agent is removed, and wherein no stabilizer and no sequestering agent are used.

15. The process as claimed in claim 14, wherein the reaction is carried out at a temperature of 40 to 60° C.

16. The process as claimed in claim 14, wherein the pressure at the end of the reaction reaches 4 to 7 bar.

17. The process as claimed in claim 14, wherein the introduction of the water is started when 10–20% of the amount by weight of the quaternizing agent of formula (II) necessary for the reaction has been added.

18. The process as claimed in claim 14, wherein the introduction of the remaining DAMEA is started when 30–70% of the amount by weight of the quaternizing agent of formula (II) necessary for the reaction has been added.

19. The process as claimed in claim 14, wherein the quaternizing agent is introduced over a period of time of 1–7 hours, the water over a period of time of 1–8 hours and the remaining DAMEA over a period of time of 2–8 hours.

20. The process as claimed in claim 1, wherein the reaction is carried out with a molar ratio of the quaternizing agent to the DAMEA of 1 to 1.1.

21. The process as claimed in claim 1, wherein the reaction is carried out with a mean ratio of water/quaternizing agent throughput of 0.2–1.5; a mean ratio of remaining DAMEA/quaternizing agent throughput of 2.5–5; and a mean ratio of water/remaining DAMEA throughput of 0.2–1.2.

22. The process as claimed in claim 1, which results in an aqueous solution having a concentration of quaternary salt of formula (I) of 50 to 85% by weight.

23. The process as claimed in claim 1, wherein the reaction is carried out with a molar ratio of the quaternizing agent to the DAMEA of 1 to 1.05.

* * * * *